United States Patent [19]

Blake et al.

[11] Patent Number: 5,202,232
[45] Date of Patent: * Apr. 13, 1993

[54] IGA BINDING PROTEIN

[75] Inventors: Milan Blake; Emil Gotschlich, both of New York, N.Y.; Gregory J. Russell-Jones, E. Roseville, Australia

[73] Assignee: The Rockefeller University, New York, N.Y.

[*] Notice: The portion of the term of this patent subsequent to Jul. 12, 2005 has been disclaimed.

[21] Appl. No.: 759,866

[22] Filed: Sep. 16, 1991

Related U.S. Application Data

[63] Continuation of Ser. No. 217,822, Jul. 12, 1988, abandoned, which is a continuation of Ser. No. 829,708, Feb. 13, 1986, Pat. No. 4,757,134, which is a continuation-in-part of Ser. No. 446,319, Dec. 2, 1982, abandoned.

[51] Int. Cl.$^5$ .................. G01N 33/535; G07K 13/00
[52] U.S. Cl. ........................ 435/7.1; 530/350; 530/387.1; 530/413
[58] Field of Search .............. 435/7; 530/350, 387, 530/413

[56] References Cited

U.S. PATENT DOCUMENTS 4,582,699  4/1986  Murray ............................. 424/1.1
4,795,702  1/1989  Blake ................................. 435/7

Primary Examiner—Robert J. Hill, Jr.
Assistant Examiner—Shelly J. Guest
Attorney, Agent, or Firm—Wyatt, Gerber, Burke and Badie

[57] ABSTRACT

Describes IgA binding protein isolatable from Group B streptococci, methods of isolation and use in immunological testing procedures.

4 Claims, No Drawings

IGA BINDING PROTEIN

This application is a continuation of application Ser. No. 07/217,822 filed Jul. 12, 1988 which is a continuation of application Ser. No. 06/829,708 filed Feb. 13, 1986, now U.S. Pat. No. 4,757,134 which is a continuation-in-part of application Ser. No. 06/446,319 filed Dec. 2, 1982. Applications Ser. Nos. 07/217,822 and 06/446,319 are now abandoned.

This invention is concerned with an IgA binding protein isolatable from selected group B streptococci, with methods of isolating the same and with use of the protein for various purposes including testing of mammalian body fluids for the presence of Neisseria infections.

IgA, as is known, is an immunoglobulin or class of antibody which is related to immunity against infections with bacteria and viruses at mucosal surfaces. It is present in all mammalian secretions including saliva, milk and vaginal washings.

Like all human antibodies, IgA is comprised of heavy and light chains, and is characterized by a constant fraction, Fc, and a variable fraction, Fab. There are two subclasses of IgA. These are $IgA_1$ and $IgA_2$. They differ in the structure of the heavy chains. Additionally, the antibodies exist in monomer form (molecular weight about 160,000), and dimer form in serum. Only the dimer form exists in mammalian secretions, and this is attached to an additional moiety known as the secretory piece. The IgA antibody, like all antibodies, is produced by the lymphocytes of the immune system. The secretory piece is produced by the epithelial cells lining the surface of body structures such as the breast, gut, salivary glands or genitourinary tract. The IgA produced by the lymphocytes is picked up by the epithelial cells from the side in contact with the circulating blood, the secretory piece is added, and the secretory IgA is secreted on the exterior surface of the epithelial cell.

In the course of combatting bacterial and viral infections, IgA participates in the neutralization of antigens by routes which are known and understood. Many clinical tests for the presence of infection have been devised and are widely utilized which depend upon recognition of an interaction between IgA and antigens generated by the infection.

Group B streptococci are a class of microorganisms which has been extensively studied and classified. No member of this class has ever been known to bind IgA. It has now been discovered that certain of these streptococci, generally of the Ib or Ic serotype will bind IgA. Moreover, procedures have been discovered for separating the IgA binding protein (IgABP) from the surface of group B streptococci where it occurs.

One such procedure is to heat the streptococci in dilute aqueous mineral acid at 50° C. to 60° C. for from 1.5 to 2.5 hours. The preferred acid is dilute hydrochloric acid, e.g., 0.15 to 0.25M, but other dilute mineral acids may be employed. The preferred procedure is to heat for two hours at 56° C. in 0.2M hydrochloric acid. The solution is neutralized with dilute alkaline reagent, e.g., 0.2M sodium hydroxide. The desired product may be precipitated by the addition of trichloroacetic acid or other reagent and then purified.

An alternative procedure is to mix the streptococci in a dilute solution of a non-ionic detergent for a period of from about 36 to 72 hours, preferably 40 to 50 hours. The protein is precipitated with a reagent such as ethanol. It may be further purified.

The preferred procedure for isolating the IgABP of this invention is by boiling in an anionic detergent.

Suitable non-ionic detergents for use in this invention include Triton x-100 and Tween 20. Both are well known and available commercially. The former is a polyethylene glycol p-isooctylphenyl ether. The latter is polyoxyethylene sorbitan monooleate. The presently preferred anionic detergent is the commercially available sodium dodecyl sulfate (SDS). Others are known and can be used.

The presently preferred procedure for isolating the IgABP of this invention using anionic detergent is as follows:

10 ml of the Group B streptococcal strain H36B/5 was grown to late-log phase in Todd-Hewitt broth. The bacteria were pelletted by centrifugation and then boiled in 1 ml. of 2% SDS in water, for 10 minutes.

The bacteria were removed by centrifugation and the proteins in the supernatant were precipitated by the addition of 0.5 ml of 30% tricloroacetic acid. The pellet obtained by centrifugation was washed once with ethanol and once with acetone. The remaining pellet was suspended in 25 ||1 of the standard SDS-PAGE boiling solution and subjected to electrophoresis in a 10% polyacrylamide slab gel. After staining with Coomassie brilliant blue and destaining, the SDS-PAGE pattern consisted predominantly of a single band with SDS-PAGE mobility corresponding to a protein of 132,000 molecular weight. A number of other minor bands with molecular weights ranging from 40,000 to 132,000 were also apparent.

A second preparation of the protein was also subjected to SDS-PAGE followed by western blotting onto nitrocellulose strips. The strip was then soaked in 0.05% Brij 35 and 5% Bovine serum albumin for 30 minutes, after which $1 \times 10^7$ cpm of $^{125}$I-labelled IgA at a concentration of 4 μg/ml was added to the strip for 4 hours. The strip was subsequently washed extensively with 0.05% Brij 35 and used to expose photographic film. By this technique it could be shown that the major protein band seen in the SDS-PAGE and some of the minor proteins were also capable of binding the $^{125}$I-IgA thereby exposing the photographic film. The minor proteins are derivatives and degradation products of IgAP which arise during isolation. Some of them bind to IgA because they still carry the IgA determinant of the original IgAP.

Molecular weight markers used in estimation of the molecular weight of the IgAPB were as follows: β galactosidase (136K), human transferrin (80K), ovalbumin (45K), cytochrome C (12.5K).

SDS-PAGE is a well known and widely used process for separating proteinaceous materials using sodium dodecyl sulfate and polyacrylamide gel electrophoresis.

The procedures for separating the IgABP of this invention from the Group B streptococci all involve extraction of the products in an aqueous medium containing a material which disrupts the attachment of the protein to the cellular surface such as dilute acid or a detergent. Extraction preferably takes place while the growth is in the log phase. The derived material is separated from the extract by precipitation with a protein precipitating reagent, preferably ethanol. Once the material is separated from the streptococcus substrate it may be isolated and purified as described herein. Alternatively, solutions of the products in relatively dilute or impure states can be utilized.

Three procedures have thus far been described for isolating the useful products of this invention. The purified product as isolated by SDS-PAGE is a protein with a molecular weight of about 132,000.

The IgABP of this invention is a cell wall bound protein which as isolated by SDS-PAGE has a molecular weight of about 132,000. The ability of the IgABP to bind IgA is destroyed by hydrolysis, for example by hydrolysis with proteases. This was established by the Western blot technique. In the test, untreated and protease digested IgABP was submitted to SDS-PAGE and electroblotted onto nitrocellulose. The blots were allowed to react with pure IgA, washed and the bound IgA, detected with an alkaline phosphatase conjugated goat immunoglobulin specific for human IgA.

It was found that the ability to bind IgA, was destroyed by the following proteolytic enzymes:
chymotrypsin
leucine amino peptidase
clostripain
papain
Streptomyces protease.

The N-terminal sequence of IgGBP was determined by automatic Edman degradation on a Beckman sequencer according to standard methods. The sequence of the first thirteen amino acids was found to be Ser-Lys-Leu-Val-Lys-Asp-Lys-Leu-Val-Lys-Thr-Lys-Glu The following table sets forth the amino acid composition as determined by automated amino acid analysis following acid hydrolysis of pure IgABP.

TABLE 1

Amino Acid Analysis of IgA Binding Protein

| Amino Acid | NMoles | ng | residues/ 100 | residues/ 130,000 MW |
|---|---|---|---|---|
| Asp | 5.518 | 634.57 | 13.8 | 158 |
| Thr | 2.830 | 285.83 | 7.08 | 81 |
| Ser | 2.059 | 179.13 | 5.15 | 58 |
| Glu | 7.134 | 920.29 | 17.8 | 204 |
| Pro | 1.986 | 192.64 | 4.97 | 57 |
| Gly | 1.274 | 72.62 | 3.19 | 37 |
| Ala | 2.160 | 153.36 | 5.40 | 62 |
| Val | 2.640 | 261.36 | 6.60 | 75 |
| Met | 0.627 | 82.13 | 1.57 | 18 |
| Ile | 1.829 | 206.67 | 4.58 | 52 |
| Leu | 3.020 | 341.26 | 7.56 | 86 |
| Tyr | 0.806 | 131.37 | 2.01 | 23 |
| Phe | 0.960 | 131.52 | 2.40 | 27 |
| His | 0.913 | 125.08 | 2.28 | 26 |
| Lys | 5.523 | 706.94 | 13.8 | 158 |
| Arg | 0.681 | 106.23 | 1.70 | 19 |

In this application and in the claims, the standard abbreviations are used to designate the amino acids. Thus, Asp is aspartic acid, Gly is glycine, etc.

No IgA binding protein has ever been reported, much less isolated, from Group B streptococci.

The salient features of the novel IgABP of this invention can be employed in two distinct solid phase systems. In one such system the binding protein is absorbed on a solid phase support as in column chromatography. The second major application is to bind the IgABP to an absorbing surface such as a plastic plate, more specifically, a test well for use in a class of assays commonly known as the enzyme linked immunosorbent assay or ELISA.

The utilities for the first type of support are:

1. The IgA binding protein as a solid phase absorbent can be used to remove IgA of all classes from serum or any other human fluid. The eluate will be devoid of IgA. This is of value when one wishes selectively to remove antibodies of the IgA class from a secretion or serum. The IgA immunoglobulins can be removed from the solid phase support in highly purified form and used for any desired purpose.

2. The IgA binding protein as a solid phase absorbent can be used to determine the antigen specificity of IgA antibody. An antigen mixture which is labelled with radioactivity is exposed to the serum or secretion containing the IgA antibody. After antigen-antibody binding has been allowed to take place the solid support is added and binds only IgA antibody and any antigen that may be specifically bound to the IgA. The solid support is washed extensively and the quantity of antigen that is bound is identified by radioactivity. The nature of the bound antigen can be tested by performing a gel electrophoretic analysis followed by autoradiography or fluorography.

The applications for the second type of support (plastic plate) are:

1. The IgA binding protein can be used to determine the concentration of IgA in serum or in a secretion. One strategy is to use a polystyrene or other plastic plate and absorb the IgA binding protein to the surface. After suitable washing, the plate is exposed to various dilutions of the fluid to be tested and after appropriate incubation is washed. The bound IgA is detected by an antibody specific for L chains (light chains) which has been conjugated to the enzyme alkaline phosphatase. The presence of this enzyme, and thus the L chains, is detected by release of the chromophore para-nitrophenol from para-nitro-phenyl phosphate.

2. The IgA binding protein can be used as a detection system for the presence of gonorrhea. The principle is that the pathogenic gonococcus elaborates an enzyme capable of cleaving human IgA of the $IgA_1$ subclass in the middle of the molecule at a region known as the hinge region. This results in the production of three fragments, the Fc portion of the molecule and two identical Fab fragments. The latter contain the L chains of the intact $IgA_1$ molecule. The test is carried out by coating a plastic plate with the IgA binding protein. The plate, after washing, is exposed to human $IgA_1$ immunoglobulin. After washing the secretion or vaginal washing is added to the wells and allowed to incubate. After the washing has been completed the plate is exposed to alkaline phosphatase conjugated anti-light chain antibody and developed with the phosphatase substrate p-nitrophenyl phosphate. If the secretion contained active IgA protease, then the Fab portions will have been cleaved from the molecule and the light chains lost from the well. A low color yield is thus an indication for the presence of the $IgA_1$ protease.

3. The IgA binding protein can be used to determine the presence of bacterial meningitis caused by *Neisseria meningitidis, Haemophilus influenzae,* and *Diplococcus pneumoniae.* All of these organisms produce a similar $IgA_1$ splitting protease. The test will be carried out exactly as described in section 2 except that the presence of the enzyme will be assayed in spinal fluid obtained by lumbar puncture which is performed routinely on patients suspected of having meningitis.

4. The IgA binding protein can be used to determine specific reactivity of antibodies of the IgA class. Since IgA is the major protective antibody found on the epithelial surfaces of the human body it is of major importance to be able to measure the IgA which is reactive with specific bacterial or viral antigens. This can be accomplished by using the IgA binding protein to coat the plates. The plates are allowed to bind. After washing a detection system for the presence of the antigen is used, for instance an antibody to the bacterial product or virus in question, and this is coupled to an enzyme or radioactive detection system.

5. The IgA binding protein can be used to determine IgA antibodies specifically in each of the two subclasses, $IgA_1$ and $IgA_2$. The manner in which this is accomplished is that the same test outlined in item 4 is used except that before the specific antigen is added the $IgA_1$ antibodies fixed to the plate are destroyed with purified gonococcal or other $IgA_1$ protease. The difference in reactivity between test according to protocol 3 and 4 allows one to determine the contribution of antibodies in each subclass.

Those skilled in the art to which this invention pertains, once they have understood the procedures for isolating and identifying the IgABP of this invention as described herein, will readily understand how it can be utilized in each of the procedures described above. They will of course recognize that it is not essential to isolate and purify the IgABP in order to practice the various embodiments of the invention. In fact it will almost always be most convenient to utilize compositions containing the binding protein at various concentrations, for example the effluent from a chromatographic column containing the binding protein in solution. One such solution can be prepared by the following procedure.

A suspension of Group B streptococci is first tested to be certain that it will bind to IgA. This may be determined by incubating a pellet of streptococci with radiolabeled IgA at room temperature for about 20 minutes and then testing by conventional procedures for the presence of conjugated IgA. Specific known strains of Group B streptococci which are known and publicly available and may be employed in the practice of this invention are A 909, F 345-3 and H 36B-5. The first two strains are 1c serotype. The last strain is 1b serotype.

A suspension of the selected strain in the log phase is extracted by boiling in 1% to 10% aqueous sodium decyl sulfate for 10 minutes to two hours at a pH of from about 6 to 9. The pH is not critical, but it is convenient to maintain it in this range with a suitable buffer such as 0.1M Tris-HCL. The bacteria are separated, for example by centrifugation. The protein remains in solution and may be precipitated by conventional procedures, including for example the addition of ammonium sulfate, ethanol, or other protein precipitating reagent.

It is most convenient to effect precipitation by the addition of ethanol at a temperature of about 0° C. to 10° C. to provide a mixture which is 60% to 90%, preferably 65% to 75% in ethanol.

The precipitated material is resuspended in water at a pH of from about 5.5 to 6.5 maintained by a suitable buffer such as glycine-hydrochloric acid, sodium acetate-acetic acid, or a citrate buffer. A 10 mM citrate buffer at pH 5.5 is most convenient. To remove the contaminating DNA or RNA, both of which are negatively charged, at this pH, the solution is passed over a DEAE-Sepharose column which has been equilibrated with the same buffer employed in solubilizing the precipitate. The absorbant is positively charged and readily binds the DNA and RNA. The effluent from the column contains the binding protein in solution in sufficient concentration to be useful for the various purposes outlined above.

DEAE-Sepharose is available from Pharmacia Fine Chemicals. It is a bead formed gel formed from agarose and converted to the diethylamino ethyl (DEAE) derivative. Other amionic exchange resins can be used.

As a further aid towards understanding this invention, the procedure for detecting a Neissera gonorrhea or meningitidis infection will now be described in more detail.

A constitutive extracellular enzyme, $IgA_1$ protease is released from the pathogenic Neisseria, *N. meningitidis* and *N gonorrhoeae*, the causative agents of Neisserial meningitis and gonorrhea respectively. This enzyme cleaves human $IgA_1$ into two fragments, the Fc fragment and the Fab fragment. An ELISA assay utilizing the IgABP isolated from group B streptococci has been developed in accordance with this invention which allows for the detection of the protease and, hence, for the presence of the Neisseria pathogens.

In this assay, the IgABP (bound to an ELISA plate) is used to bind the Fc portion of IgA. The $IgA_1$ protease can then cleave the IgA and release the Fab fragments which contain L-chains. The presence or absence of the light chains (corresponding to the absence or presence of the enzyme) can then be detected using a suitable reagent.

The assay is as follows:

1. IgABP (1–5 μg/ml in 0.1M Tris HCl pH 9.8) is used to coat the surface of an ELISA plate with 100 μl/well at ambient temperature (20° to 40° C.) for about 10 to 16 hours.

2. The plate is washed 6 times with a solution of 0.02 to 0.2% Brij in 0.9% NaCl, i.e., isotonic sodium chloride.

3. IgA (0.2 to 250 μg/ml in 10 mM Tris HCl pH 7.5 may be from 5 to 10. After one hour solutions containing the $IgA_1$ protease (vis: vaginal secretions) are added to the IgA and allowed to react for 15 minutes to 4 hours at ambient temperature.

4. The plate is washed as described above.

5. Alkaline phosphatase conjugated anti-human light chain serum is than added to each well and incubated at least 30 minutes and preferably 1 to 2 hours at ambient temperature.

6. The plate is washed as in 2.

7. The alkaline phosphatase substrate, para nitrophenol phosphate, suitably in a buffer at a pH of at least 7, and preferably 9 to 10 is added to each well and allowed to incubate for at least 30 minutes, suitably up to 2 hours at ambient temperature.

8. The $OD_{405}$ is then determined.

$IgA_1$ protease negative wells still contain intact IgA and so give a yellow color on reaction with the substrate. $IgA_1$ protease positive wells do not contain intact IgA, and so do not give a color reaction on addition of the substrate.

Brij 35 is a non-ionic detergent comprising polyoxyethylene ethers of fatty acids. It is used to protect the absorbing surface from non-specific absorption of extraneous proteins. The magnesium chloride is not essential, but is preferred expecially if phosphate buffers are employed since the $IgA_1$ protease requires trace amounts of magnesium ions for optimum activity.

It will be apparent to those skilled in the art that at each step of the procedure variations can be made in such parameters as concentration, temperature and incubation time without adversely affecting the test. Equivalent buffers may be employed.

What is claimed is:

1. A method of detecting a pathogenic *Neisseria meningitides* or *Neisseria gonorrhoeal* infection characterized by the presence of an IgA protein in a body fluid which comprises the steps of:

A. exposing an absorbing surface to a solution of an IgA binding protein which is characterized as having a molecular weight of about 132,000 when determined by sodium dodecyl sulfate polyacrylamide gel electrophoresis, reacting specifically with the Fc portion of the human IgA, hyrolyzable by protease, containing the following amino acids in the residues per 130,000 molecular weight indicated:

| Asp | 158 | Thr | 81 | Ser | 58 |
   |-----|-----|-----|----|-----|-----|
   | Glu | 204 | Pro | 57 | Gly | 37 |
   | Ala | 62  | Met | 18 | Val | 75 |
   | Ile | 52  | Leu | 86 | Tyr | 23 |
   | Phe | 27  | His | 26 | Lys | 158 |
   |     |     | Arg | 19 |     |     | the N-terminal amino acid sequence, as determined by Edman degradation, being Ser-Lys-Leu-Val-Lys-Asp-Lys-Leu-Val-Lys-Thr-Lys-Glu-, at a pH of from 6 to 11 at ambient temperature to coat the absorbing surface with said binding protein, B. washing the surface with aqueous isotonic sodium chloride solution containing a non-ionic detergent, C. exposing the surface to an aqueous solution of IgA at a concentration of 0.2 to 250 ug/ml at pH 5 to 10 thereby to bind the IgA to the binding protein on the absorbing surface, D. incubate a secretory fluid from the mammal suspected of harboring the infection for 15 minutes to 4 hours at ambient temperature, E. washing the surface as in step 2, F. incubating with alkaline phosphate conjugated anti-human light chain serum for at least 30 minutes at ambient temperature, G. washing the surface as in step 2, H. incubating with para nitrophenol phosphate in a buffer at a pH of at least 7 for 5 to 60 minutes at ambient temperature, and I. determining the optical density of the resulting medium at 405 nm.

2. A method as in claim 1 wherein the solution of step C contains magnesium chloride.

3. A product comprising an IgA binding protein absorbed on a solid support, said protein being isolatable from Group B streptococci, capable of binding IgA, and further characterized as having a molecular weight of about 132,000 when determined by sodium dodecyl sulfate polyacrylamide gel electrophoresis, reacting specifically with the Fc portion of the human IgA, hydrolyzable by protease, containing the following amino acids in the residue per 130,000 molecular weight indicated:

| Asp | 158 | Thr | 81 | Ser | 58 |
   |-----|-----|-----|----|-----|-----|
   | Glu | 204 | Pro | 57 | Gly | 37 |
   | Ala | 62  | Met | 18 | Val | 75 |
   | Ile | 52  | Leu | 86 | Tyr | 23 |
   | Phe | 27  | His | 26 | Lys | 158 |
   |     |     | Arg | 19 |     |     | the N-terminal amino acid sequence, as determined by Edman degradation, being Ser-Lys-Leu-Val-Lys-Asp-Lys-Leu-Val-Lys-Thr-Lys-Glu.

4. A product as in claim 3 wherein the solid support is a solid base for use in column chromatography.

* * * * *